United States Patent [19]

Altvater

[11] Patent Number: 5,782,635
[45] Date of Patent: Jul. 21, 1998

[54] DEVICE FOR WORKING A SURFACE

[76] Inventor: Axel Altvater, Sindelfinger Strasse 33, Sindelfingen 71069, Germany

[21] Appl. No.: 737,306
[22] PCT Filed: Apr. 25, 1995
[86] PCT No.: PCT/EP95/01551
  § 371 Date: Oct. 25, 1996
  § 102(e) Date: Oct. 25, 1996
[87] PCT Pub. No.: WO95/28893
  PCT Pub. Date: Nov. 2, 1995

[30]  Foreign Application Priority Data

Apr. 27, 1994 [DE] Germany ............... 44 14 610.8

[51] Int. Cl.[6] ............................................. A61C 17/00
[52] U.S. Cl. ................ 433/143; 433/166; 433/173
[58] Field of Search .......................... 433/143, 165, 433/166, 172, 173

[56]  References Cited

U.S. PATENT DOCUMENTS 4,795,344  1/1989  Brewer, Jr. .................. 433/143
5,244,390  9/1993  Lazzara et al. ............... 433/143

*Primary Examiner*—John J. Wilson
*Attorney, Agent, or Firm*—Darby & Darby

[57]  ABSTRACT

A device is proposed for cleaning the surface of inserted oral implants and/or the abutments placed thereon. The device is distinguished by the provision of a cleaning curette (31, 131) which at least partially covers the surface to be cleaned.

17 Claims, 3 Drawing Sheets

DEVICE FOR WORKING A SURFACE

BACKGROUND OF THE INVENTION

The invention concerns a device for working the surface of inserted oral implants and/or the abutments placed thereon and the like.

Implants of the type addressed here must be cleaned at regular intervals whereby scalers or curettes preferably made of synthetic material are used. The disadvantage in this is that cleaning is very complicated and not sufficiently effective. Particularly deep subgingival parts cannot be reached in this manner.

OBJECT OF THE INVENTION

Therefore, it is the object of the invention to create a device of the above mentioned type that does not have these disadvantages.

A device for treating cleaning a surface is proposed for attaining this object that has the features cited in claim 1. Due to the fact that a cleaning curette is provided which at least partially covers the surface of the implant or the abutment, planer cleaning is guaranteed that is considerably more thorough than is the case with conventional methods.

An embodiment of the device is preferred in which the cleaning curette is formed as a bushing that has at least one slot. An edge of the slot serves quasi as a cutter that removes substances that are deposited on the surface of the implant or the abutment. The curette is thereby constructed very simply and, thus, can be realized in a cost-effective manner. The embodiment guarantees thorough cleaning of the affected surfaces.

In addition, an embodiment of the device is preferred in which the slot in the bushing runs approx. along an imaginary helical line that is arranged in such a way that the removed substances are discharged by a rotation of the cleaning curette in the oral cavity.

Particularly preferred is an embodiment of the device in which the cleaning curette is formed as a rotationally symmetrical part and can be attached to the implant or the abutment. This produces an especially simple and simultaneously very intensive cleaning of the surfaces particularly in the cleaning of rotationally symmetrical implants and abutments.

In addition, an embodiment of the device is preferred in which the cleaning curette can be placed on a receptacle that considerably simplifies the handling of the curette and, if necessary, can also be coupled with a mechanical driving gear.

An additional embodiment of the device is distinguished by the fact that a guide can be placed on the implant or abutment to be cleaned onto which guide the cleaning curette can be attached and thereby be easily brought up to the surfaces that are to be cleaned.

Additional embodiments are yielded from the remaining sub-claims.

The invention is explained in the following on the basis of the drawings. These show:

DETAILED DESCRIPTION OF THE INVENTION

Figure 1:
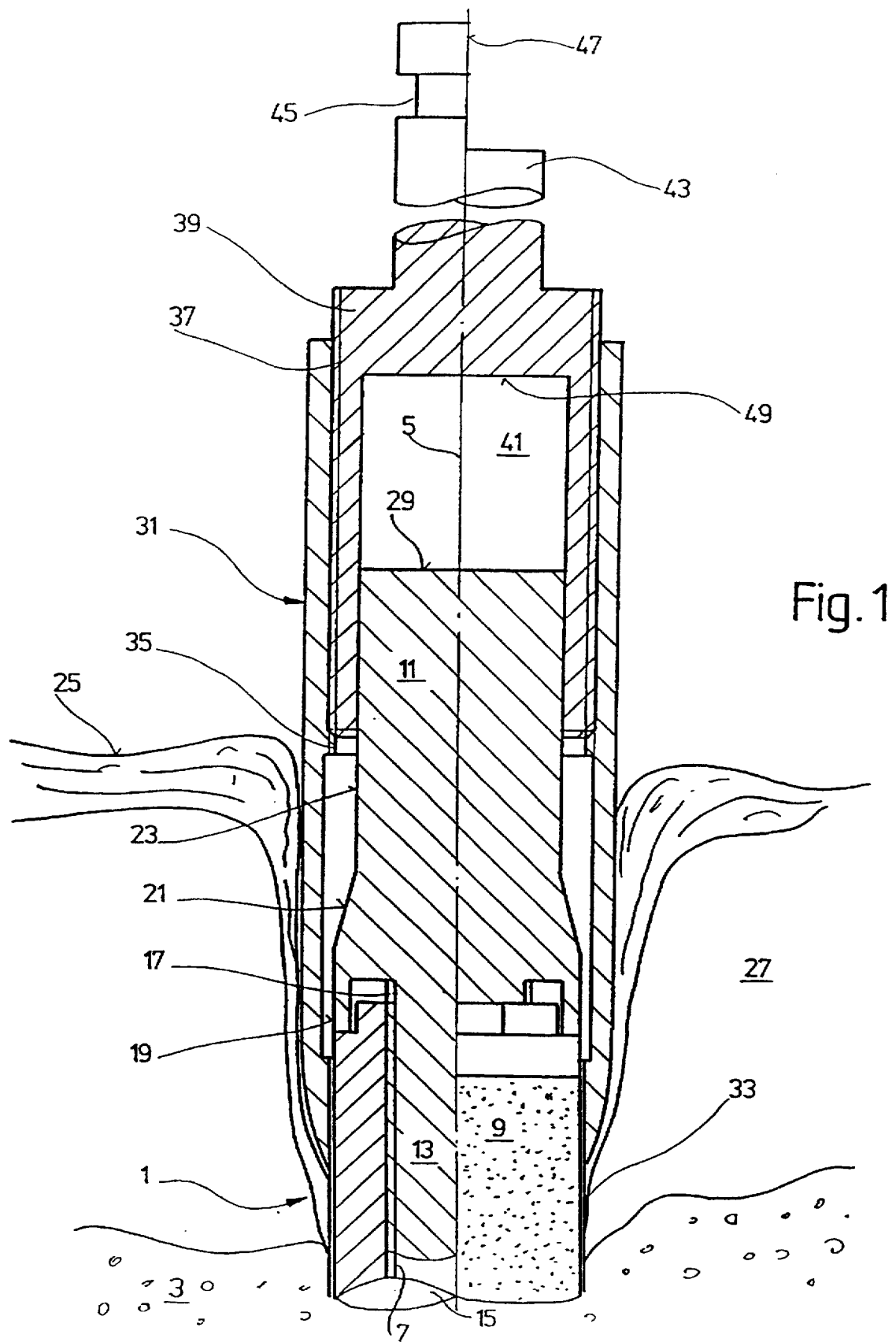
FIG. 1 A longitudinal partial section through a first embodiment of a device for cleaning a surface that is attached to an implant.

In the sectional representation in FIG. 1, one can recognize an implant that is inserted into a jawbone 3. The implant 1 is formed to be rotationally symmetrical. The half of the implant 1 that lies to the left of the center line 5 is reproduced in a longitudinal section and that which lies to the right of this line is reproduced as a side view. The representation in FIG. 1 shows only the upper end of the implant 1 which continues into the jawbone 3.

The implant 1 is formed at least in its upper area as a hollow body or bushing and is provided with an internal screw thread 7. The exterior of the implant 1 can be provided with a biologically compatible coating 9 for instance one made of titanium plasma.

A guide pin 11 that serves as a guide is provided above the implant 1, which guide pin, for its part, is preferably formed to be rotationally symmetrical and engages with a threaded pin 13 in a hollow area 15 of the implant 1. It is provided with an external screw thread 17 that works together with the internal screw thread 7 of the implant 1 and guarantees a secure anchorage of the guide pin 11 on the implant 1.

In the area of the guide pin 11 adjacent to the implant 1, the first outer surface 19 of the guide pin, as well as that of the implant 1, is formed cylindrically, whereby the outside diameter of this first outer surface 19 and that of the implant 1 conform. The outer surface 21 of the guide pin 11 is formed conically above the cylindrical first outer surface 19, so that a truncated cone surface area is yielded here to which a further cylindrical second outer surface 23 is adjoined whose external radius is smaller than that of the first outer surface 19.

It is evident from FIG. 1 that the implant 1 projects somewhat beyond the surface of the jawbone 3, but not up to the surface 25 of the gums 27. The length of the guide pin 11 is selected so that its end 29 that is turned away from the implant 1 projects over the surface 25 of the gums 27.

Over the guide pin 11, a cleaning curette 31 is turned upside down, whose length is selected so that it penetrates the gums 27 and the upper part of the implant 1 projecting out of the jawbone 3 at least covers over a certain distance, but does not touch the jawbone 3, however. The cleaning curette 31, for its part, is formed as a sheath that tapers conically at its lower end that faces the jawbone 3 and thereby can forge ahead to the outer surface 33 of the implant 1 without damaging the gums 27. The inside diameter of the cleaning curette 31 is selected in such a way that it abuts the outer surface 33 of the implant 1 and exerts a certain force on this.

An internal screw thread 35 is provided in the upper area of the sheath into which a receptacle 39 that is provided with a external thread screw 37 engages.

The receptacle 39 is formed as a sheath which encloses an interior space 41. Its inside diameter is adapted to the outside diameter of the second outer surface 23 of the guide pin 11 in such a way, that this serves as a guide for the receptacle 39, so that the receptacle 39 together with the cleaning curette 31 on the guide pin 1 [sic] can be subjected to a rotational motion.

The receptacle 39 continues on its end that is turned away from the implant 1 into a receptacle pin 43, which works together with a suitable manipulator that can consist for instance of a turning knob, a manual cap or an elbow allocated to a drill.

It is provided, for example, with a groove 45 placed in its outer surface in order to guarantee a coupling with the manipulator. The uppermost half of the receptacle pin 43 is removed in order to guarantee favorable positive locking for transmitting the required moment of torsion, so that a corresponding bearing surface 47 is yielded.

It is preferred that the interior space 41 of the receptacle 39 be formed cylindrically. It extends so far into the receptacle 39, that, when sliding the receptacle 39, the guide pin 11 hits the base 49 of the interior space 41 at the earliest when the cleaning curette 31 has reached the work position shown in FIG. 1.

Figure 2:
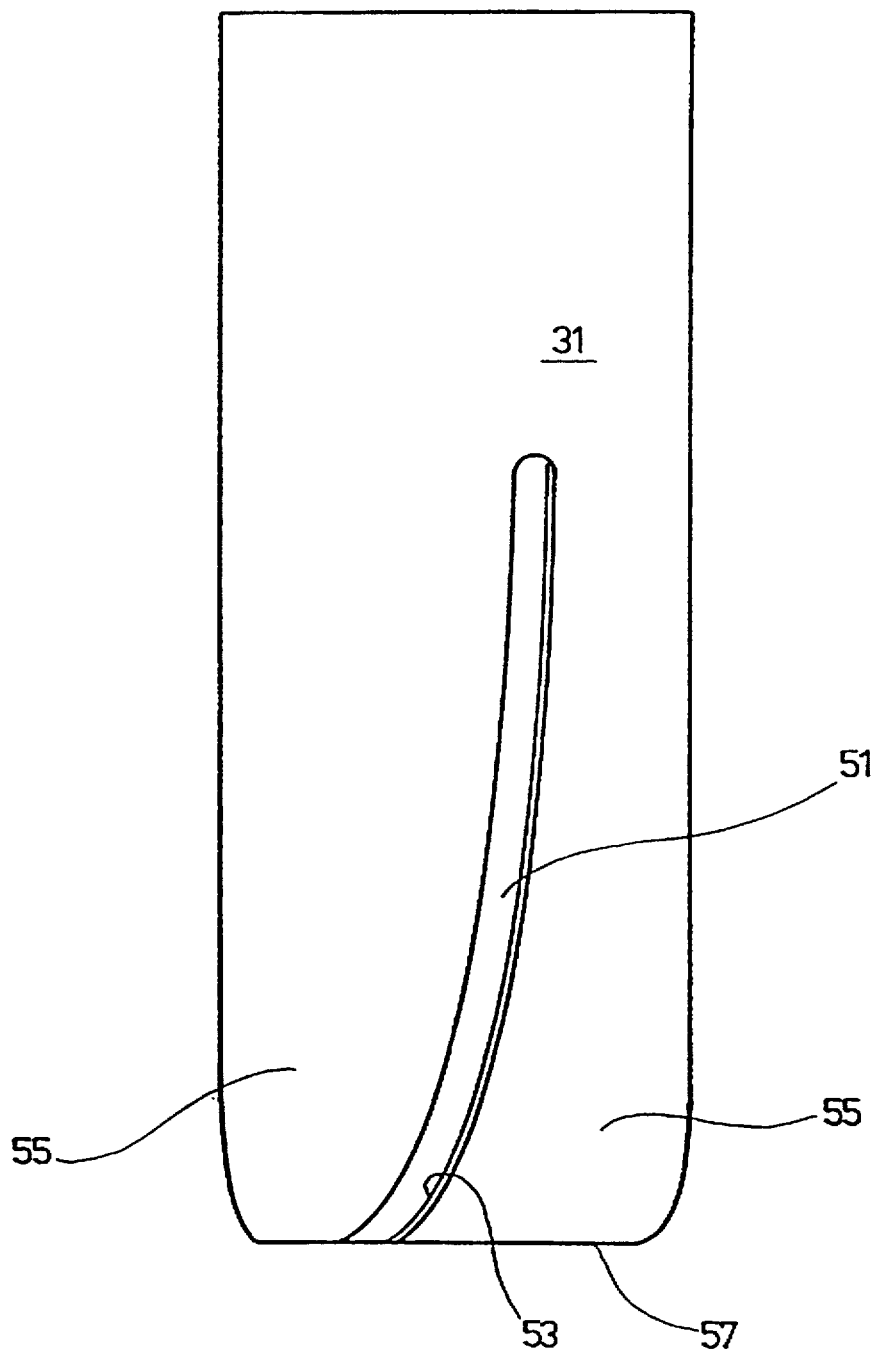
FIG. 2 A side view of a cleaning curette as per FIG. 1.

FIG. 2 shows a side view of the cleaning curette 31. A through slot 51 placed in the wall of the cleaning curette 31 can be identified there which follows a helical line and whose one edge is used as a cutter 53. The approximately helical course of the slot 51 is advantageous particularly in the lower area of the cutter 53, because substances removed from the outer surface 33 of an implant 1 by the cutter 53 are still conveyed away upwardly and, in this way, make their way into the oral cavity of the patient. The length of the slot 51 shall at least be selected in such a way that the substances removed from the implant 1 can at least be discharged so far upwards in the direction towards the mouth cavity that easy rinsing is possible.

The cleaning curette 31 is shown in a simplified form here. Preferred are embodiments with, for example, three slots 51 that each delimit a cleaning finger 55.

The following must be noted on the functioning of the cleaning curette 31:

In order to carry out cleaning of the outer surface 33 of the implant 1, fastening elements applied to the implant 1 are removed and the guide pin 11 is screwed on. Due to the fact that this projects beyond the surface 25 of the gums 27, the position of the implant 1 is easily recognizable. The cleaning curette 31 can now be slid onto guide pin 11 until the desired working depth has been reached. In order to avoid damage to the jawbone 3, the inside of the hollow space 41 can be provided with a projection that works together with the upper end 29 of the guide pin 11. It is also possible to pull the base 49 of the hollow space 41 so far down that this hits the upper end of 29 of the guide 11 when the desired working depth has been reached. If necessary, the bone can also be removed up to a definable depth.

Cleaning of the outer surface 33 of the implant 1 can be carried out using an up and down movement of the cleaning curette 31. It then requires a subsequent step for the elimination of the substances removed from the outer surface 33. With this type of cleaning, a lower edge 57 of the cleaning curette 31 is used to clean the outer surface 33.

Preferred, however, is a rotationally symmetrical arrangement of the guide pin 11 as well as the cleaning curette 31 that is then designated as a rotating curette as well as the receptacle 39. Due to the helical arrangement of the slot 51, substances that are removed by the cutter 53 and those that are loosened from the outer surface 33 are discharged upwardly into the mouth cavity. During cleaning of the outer surface 33 of the implant 1, a rotational motion of the receptacle 39 and thereby of the cleaning curette 31 is effected by means of the manipulator, which in doing so is guided securely onto the guide pin 11, which, due to its dimensions that are coordinated with the interior space 41, serves as a centering and quasi rotational axis for the cleaning curette 31 and prevents slanting.

Especially quick cleaning of the outer surface 33 is yielded by several slots 51.

The inside diameter of the cleaning curette 31 that is formed as a sheath is coordinated in its lower area that works together with the outer surface 33 of the implant 1, with the outer surface's outside diameter, so that the cleaning curette 31 lies under a certain initial stress on the outer surface 33 of the implant 1 and a thorough cleaning is guaranteed.

If the cleaning curette is manufactured from an elastic material, the inside diameter can also be selected to be somewhat smaller that the outside diameter of the outer surface 33. The cleaning fingers 55 are expanded then when applying the cleaning curette 31 in the area of the conical outer surface 21 and glide smoothly from the first outer surface 19 of the guide pin 11 to the outer surface 33 of the implant 1. The elastically resilient cleaning arms 55 fit securely against the outer surface 33 so that the respective cutter 53 thoroughly removes impurities.

It is evident from what has been said that an inner cone, which extends in the direction towards the lower edge 57 and thus serves as an introduction aid for the guide pin 11, can be provided in the lowermost area of the cleaning curette 31 that is formed as a sheath. As the case may be, one can then dispense with the conical outer surface 21.

In the case of the embodiment illustrated in FIG. 1, the second outer surface 23 is provided with a considerably smaller outside diameter than the first outer surface 19 of the guide pin 11, so that the cleaning curette 31 can easily be placed upon [it].

A so-called abutment (not shown here) can be placed upon the implant 1 shown in FIG. 1; this abutment preferably has a cylindrical outer surface and is fastened to the implant 1 by means of threaded pin that engages in the internal screw thread 7. For its part, the abutment has an internal screw thread into which threaded pins of any superstructure as well as just the threaded pin 13 of the guide pin 11 can engage. The outside diameter of the abutment corresponds to that of the implant 1 and that of the first outer surface 19 of the guide pin 11, so that it is possible to also clean the surface of the abutment with the cleaning curette 31 shown in FIG. 1 without further ado. Just like the implant 1, the abutment can be used to attach fastening elements to which artificial teeth or the like are anchored.

The guide pin 11 can be manufactured from a suitable synthetic material or from metal. The use of ceramics is also conceivable for manufacturing this type of a guide pin 11.

The receptacle 39 can be manufactured from any suitable material, i.e., from synthetics, metal or the like.

Synthetic material that can also be manufactured by means of an injection molding or compression molding method can be used to manufacture the cleaning curette 31. It is also conceivable to use metal or ceramics to manufacture the cleaning curette.

A metal curette is to be preferred if a particularly sharp cutter 53 is of interest. However, using a synthetic curette with a metal insert is also conceivable. The cutter 53 can be formed so that it can be resharpened.

If relatively soft substances are supposed to be removed from the surface of the implant 1 or an abutment, synthetic cleaning curettes can be used in a preferred manner. If, however, hard deposits such as calculus are supposed to be removed, a metal curette is preferred.

The cleaning curette 31 described here is not just useable for customary cleaning processes. It is also conceivable to remove the coating 9 in the uppermost area of the implant 1, which is required in particular if pathogenic germs have forged ahead to the implant 1 and have lodged in the preferably porous coating 9, so that combating the germs with drug therapy is practically precluded.

Due to the special arrangement of the edges of the slot 51 not just a removal of the coating 9 can be achieved. It is also possible to condition the smooth outer surface 33 of the implant 1 that is created in this way, hence to roughen again for depositing tissue.

The cleaning curette can be provided on its inside also with at least one internal screw thread emanating from one or several cleaning fingers, which internal screw thread is in mesh with an external screw thread of the implant or the abutment that is not shown in the figures and cleans this. As a result of this conformity, even areas with difficult accessibility and those that are hardly accessible in a conventional manner can be cleaned thoroughly.

It is possible using the device described here to compensate for the limited defense possibilities of peri-implantar soft tissue and to combat infection. In any case, deep subgingival impurities on the surface of an implant or an abutment placed thereon can be thoroughly eliminated with the cleaning curette 31 described here. Via a suitable selection of material for the rotating curette, the most varied of layers can be removed, even a coating of the implant. Cleaning curettes made of titanium tantalum alloy are preferred for removing a coating of the implant.

The cleaning curette 31 can eventually also be provided with cutters on its exterior that are used to remove tissue either in the area towards the implant 1 or from the bony tissue.

Sterilization and thus multiple use is possible via a corresponding selection of materials for the receptacle 39, the cleaning curette 31 and the guide pin 11. It is also conceivable to use all or individual parts only just once.

Figure 3:
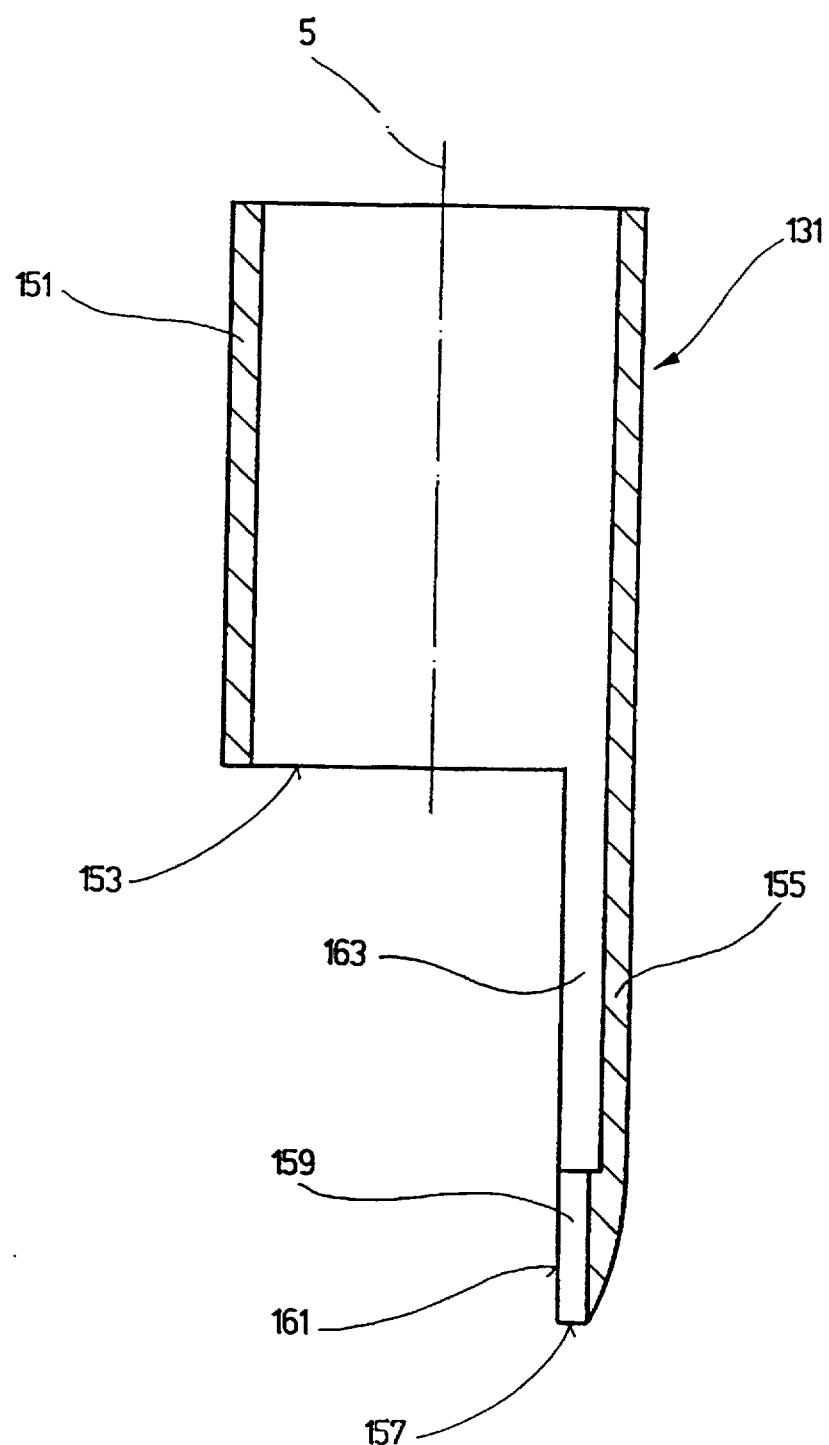
FIG. 3 A longitudinal section through the lower part of a second embodiment of a device of the type addressed here.

After everything it becomes clear that the cleaning curette 31 described here can also have a simplified design, an example of which is shown in FIG. 3, which reproduces a longitudinal section through the lower part of a second embodiment of a cleaning curette 131. The cleaning curette shown here has an essentially sheath-shaped, that is, cylindrical basic body 151, which can be connected with the receptacle 39 that was explained on the basis of FIG. 1.

The basic body 151 can be formed as a completely closed bushing or a slotted bushing.

Arising from the lower edge 153 of the basic body 151 is a cleaning arm 155, which represents practically a striated section of the cleaning curette 31 shown on the basis of FIGS. 1 and 2. The striated section shows a cleaning area 159 that is adjacent to the front side 157 of the cleaning arm 155 and whose inside represents a section of a cylinder and thus at least partially covers an implant 1 that is to be cleaned (not shown here). In this case, the cleaning area 159 has a cleaning edge 161 which corresponds to the cutter 53 of the embodiment shown on the basis of FIGS. 1 and 2. The cleaning edge here essentially runs parallel to the center line 5 of the cleaning curette 131. However, it is also conceivable that the cleaning edge 161 runs along an imaginary helical line as this was explained on the basis of FIG. 2. With this type of arrangement, the cleaning arm 155 corresponds to a cleaning finger 55 of the embodiment shown on the basis of FIGS. 1 and 2.

The cleaning arm 155 of the embodiment shown in FIG. 3 is, however, considerably narrower than the cleaning finger 55. Via a limited rotational motion of the basic body 151, narrow, defined areas of an implant 1 or an abutment can be cleaned, hence considerably smaller areas than is possible with the cleaning curette 31 shown on the basis of FIGS. 1 and 2.

The second embodiment of the cleaning curette 131 is therefore applicable particularly for special cases. A complete cleaning of the outer surface of an abutment is also possible, however, with a complete rotation of the cleaning curette 131.

In all cases, it is moreover conceivable that the cutter 53 or the cleaning edge 161 extends to the front side or the lower edge 153 of the cleaning curette 131, so that, with this type of arrangement, bone can also be removed in the direct vicinity of the implant 1, if this is required or desired.

The interior surface 163 of the cleaning arm 155 is formed rebounding above the front side 157 so that implants that are supposed to remain untreated in sections can also be cleaned.

The cleaning edge 161 then extends beginning from the front side 157 of the cleaning arm 155 just over an area in the lowermost section of the cleaning arm, while further above, in the direction towards the lower edge 153 of the basic body 151, the cleaning arm remains without contacting the implant 1 when the cleaning curette 131 is shifted into a rotational motion.

With this type of arrangement it is possible, for example, to use the cleaning edge 161 to work the surface of implants that have a screw thread in their uppermost section and are supposed to remain untreated in this area. The uppermost screw thread section of the implant 1 remains untreated due to the rebounding interior surface 163, while the part lying below this is worked by the cleaning edge 161. Due to the special arrangement of the interior surface 163 that can also be formed to be concave, implants that extend upwards can also be cleaned. The extending sections of the implants then lie within the rebounding area of the interior surface 163, while the areas lying further inside can be reached by the cleaning edge 161.

From the explanations regarding FIG. 3 is becomes clear that the basic body 151 of the cleaning curette 131 can also be provided with several cleaning arms 155 that lie at an interval from each other.

Due to the small width, the cleaning arms are formed so that they are especially resilient or elastic, so that careful working of the surface of implants is quite possible in particular.

Should the cleaning curette 131 be formed in such a way that three wide cleaning arms 155 arise from the basic body 151, whose cleaning edge 161 is arranged on an imaginary helical line, then an arrangement is essentially yielded as was shown on the basis of FIGS. 1 and 2. It is therefore evident that the cleaning curette can be adapted very variably to special application cases.

Finally, reference is still made to the fact that what was mentioned regarding the first embodiment of the cleaning curette on the basis of FIGS. 1 and 2 also applies fundamentally to the second embodiment as per FIG. 3. This affects, for example, the materials from which the cleaning curette 131 can be manufactured, but also the coupling of the cleaning curette to a receptacle 39, which was explained on the basis of the description of FIG. 1.

From the explanations of the two embodiments of the cleaning curette it becomes clear that a cleaning principle that deviates fundamentally from known curettes is being pursued here. While the surface of the implants or the like are essentially scraped clean with known hook-like curettes, whereby, even in the case of very skilled persons, one cannot preclude that wide areas of the implant surface remain untreated, in the case of a cleaning curette of the type in accordance with the invention, rotation of the curette takes place in which the entire circumferential surface of the implant is forcibly cleaned. Since its surface is partially covered, the surface is not cleaned here and there, as is the case with hook-like curettes. On the contrary, a planer cleaning of the surface of the implant takes place, in which even unskilled persons are in a position without further ado to treat all areas of the implant without leaving uncleaned surface sections. In particular with a slow forward movement of a relatively quickly rotating curette, comprehensive cleaning of the implant is guaranteed with practically 100% certainty. Therefore, very high cleaning quality is achieved even when the curette is used by unskilled persons.

We claim:

1. A device for working the surface of inserted oral members, said device comprising:
   a cleaning curette that has a sheath-shaped basic body having at least one through slot therein, the at least one through slot has at least one cleaning edge that is formed as a cutter that removes substances deposited on the surface.

2. A device in accordance with claim 1, wherein the basic body is formed as a rotationally symmetrical part and is attach able to the inserted oral member.

3. A device in accordance with claim 1, wherein the sheath has three slots, each slot having one edge that forms a cutter.

4. A device in accordance with claim 1, wherein the at least one cleaning edge extends along a helical path.

5. A device in accordance with claim 1, wherein the cleaning curette is formed as a rotationally symmetrical part and is attachable to the inserted oral member.

6. A device in accordance with claim 1, wherein the cleaning curette is made from the group consisting of synthetic material, metal or ceramics.

7. A device in accordance with claim 1, further comprising a receptacle, the cleaning curette being placed on the receptacle.

8. A device in accordance with claim 1, further comprising a guide being attached to the inserted oral member.

9. A device in accordance with claim 8, wherein the surface of the guide is rotationally symmetrical.

10. A device in accordance with claim 8, wherein the outside diameter of the guide in an area adjacent to the inserted oral member has an outside diameter that corresponds to the outside diameter of the inserted oral member.

11. A device in accordance with claim 8, wherein the surface of said guide has at least one area that is formed as a truncated cone surface.

12. A device in accordance with claim 8, wherein said guide engages an interior surface of the cleaning curette.

13. A device in accordance with one claim 8, further comprising a receptacle having an interior surface, said guide engages in the interior of the receptacle.

14. A device according to claim 1, wherein the at least one cleaning edge extends parallel to a center line of the basic body.

15. A device for treating or working the surface of inserted oral members, said device comprising:
    a cleaning curette that has a sheath-shaped basic body having at least one through slot therein wherein the cleaning curette has at least one cleaning edge that is formed as a cutter that removes substances deposited on the surface, the cleaning curette has a cleaning arm arising from the basic body, the cleaning arm has the cleaning edge.

16. A device in accordance with claim 15, wherein said cleaning arm has a concave arched interior surface that is adapted to the contour of the inserted oral member.

17. A device according to claim 15, wherein the cleaning arm includes a section between said cleaning edge and said basis body that is spaced from the inserted oral member.

* * * * *